US00PP10851P

United States Patent [19]

Utecht

[11] Patent Number: Plant 10,851

[45] Date of Patent: Apr. 6, 1999

[54] GERANIUM PLANT NAMED 'FISBEA'

[76] Inventor: Angelika Utecht, Hinterer Rebstock 38, 56410 Montabaur, Germany

[21] Appl. No.: 968,043

[22] Filed: Nov. 12, 1997

[51] Int. Cl.[6] ..... A01H 5/00

[52] U.S. Cl. ..... Plt./87.12

[58] Field of Search ..... Plt./87.12

*Primary Examiner*—Howard J. Locker

*Attorney, Agent, or Firm*—Foley & Lardner

[57] ABSTRACT

A new and distinct cultivar of geranium named 'Fisbea', particularly characterized by the combined features of bright cherry red flower color, small compact, semi-spherically shaped umbels, bright, light green foliage with weak zonation, tall but bushy and well-branched plant habit, early to medium spring flowering response, and its very floriferous habit throughout the summer.

1 Drawing Sheet

1

The present invention comprises a new and distinct cultivar of geranium, botanically known as *Pelargonium peltatum*, and referred to by the cultivar name 'Fisbea'.

'Fisbea' is a product of a planned breeding program which had the objective of creating new geranium cultivars with red flower color, vigorous growth, and well branched plant habit.

'Fisbea' was originated from a hybridization made by inventor Angelika Utecht in a controlled breeding program in Galdar, Gran Canaria, Spain in 1992. The female parent was hybrid seedling No. 361/6, derived from crossings between ivy geranium variety no. 418 from the Leuenberger collection, and the commerical varieties Yale and St. Malo 19/84. The female parent is characterized by dark red semi-double to double flowers, medium green foliage with weak zonation, and medium to vigorous growth habit. The male parent of 'Fisbea' was 'Guimo' (commercially known as Momo), characterized by single scarlet flowers, large, light to medium green leaves without zonation, good branching ability, and moderately vigorous growth.

'Fisbea' was discovered and selected as one flowering plant within the progeny of the stated cross by Angelika Utecht in 1993 in a controlled environment in Galdar, Gran Canaria, Spain.

The first act of asexual reproduction of 'Fisbea' was accomplished when vegetative cuttings were taken from the initial selection in Autumn 1993 in a controlled environment in Galdar, Gran Canaria, Spain, by, or under the supervision of, Angelika Utecht. Horticultural examination of plants grown from these cuttings initiated in May, 1994 in Hillscheid, Federal Republic of Germany, and continuing thereafter, has demonstrated that the combination of characteristics as herein disclosed for 'Fisbea' are firmly fixed and are retained through successive generations of asexual reproduction.

'Fisbea' has not been observed under all possible environmental conditions. The phenotype may vary significantly with variations in environment such as temperature, light intensity and day length, without, however, any variation in genotype. The following observations, measurements, and comparisons describe plants grown in Hillscheid, Federal Republic of Germany, under greenhouse conditions which approximate those generally used in commerical practice.

The following traits have been repeatedly observed and are determined to be basic characteristics of 'Fisbea', which in combination distinguish this geranium as a new and distinct cultivar:

1. Bright red double flowers.
2. Compact, semi-spherically shaped inflorescences.
3. Grass-green foliage with weak zonation.

2

4. Vigorous growth in combination with very good branching characteristics.
5. Early to medium flowering response and very floriferous throughout the year.

Of the many commercial cultivars known to the present inventor, the most similar in comparison to 'Fisbea' are the cultivars 'Fisrom', disclosed in U.S. Plant Pat. No. 7,567, and 'Fisrock', disclosed in U.S. Plant Pat. No. 10,365.

In comparison to 'Fisrock', 'Fisbea' has a lighter, medium red flower color, lighter green foliage, differently shaped leaves with only slight zonation, and a much more vigorous growth habit.

In comparison to 'Fisrom', 'Fisbea' has smaller flowers and umbels, differently shaped leaves, and shorter internodes. In addition, it branches more easily and is more floriferous throughout the summer.

The accompanying color photographic drawing shows typical flower and foliage characteristics of 'Fisbea', with colors being as true as possible with illustrations of this type.

In the following description, color references are made to The Royal Horticultural Society Colour Chart. The color values were determined indoors from flowers developed in a greenhouse in May 1995 in Hillscheid, Germany.

Classiification:

*Botanical.*—A hybrid of the species *Pelargonium peltatum l'Hert.*

*Commercial.*—Ivy geranium, cv. 'Fisbea'.

Inflorescence

Umbel:

*Shape.*—Nearly semi-spherical.

*Average diameter.*—75 mm.

*Peduncle length.*—149 mm.

*Pedicel length.*—20 mm.

*Pedicel color.*—Medium green, with occasional slight infusion of anthocyanin.

*Number of flowers per umbel.*—About 11–12.

Corolla:

*Average diameter.*—48 mm.

*Number of petals.*—13–18.

*Number of petaloids.*—1–3.

*Color (general tonality from a distance of three meters).*—Red to cherry red.

*Color of upper petals.*—46 B.

*Markings of upper petals.*—2 blackish stri weak.

*Color of lower petals.*—46 B.

*Color of lower surface of petals.*—46 C to 52 A.

*Color of sepals.*—Light green, occasionally slightly reddish colored.

*Number of sepals.*—Normally 5.

Bud:

*Shape.*—Narrow, elliptic.

*Color (adaxial).*—Light green.

*Color (abaxial).*—Light red, somewhat marbled.

Reproductive organs:

*Androecium.*—7 fertile anthers, white filaments, orange-yellow pollen, black lower side.

*Gynoecium.*—6-lobed dark purple stigma, white filament.

*Seed set.*—No seed set observed.

Spring flowering response period: In Hillscheid, Germany in 1995 plants had on average 0.7 flowers opened 15 weeks after planting of unrooted cuttings (pinched plants).

Outdoor flower production: The flower count in 1995 in Hillscheid, Germany indicated 135–140 umbels per plant for May through August observation period.

*Durability.*—Shatter resistance good; rain resistance good, medium heat resistance.

Plant

Foliage:

*Form.*—Ivy shaped, with open base.

*Margin.*—Mainly entire, a few notches near the tips.

*Size of leaf.*—92 mm.

*Color of upper surface.*—Light medium green ("grass green"), approximately 137 D.

*Color of zonation.*—Weak, narrow ring, brown, about 166 A; may almost disappear in summer.

*Tolerance of botrytis.*—Good.

General appearance and form:

*Internode length.*—20–40 mm.

*Branching pattern.*—10.5 branches per plant, for 16-week-old plants.

*Length of plants.*—100 cm (in September, for 35-week-old plants).

I claim:

1. A new distinct cultivar of geranium plant named 'Fisbea', as illustrated and described.

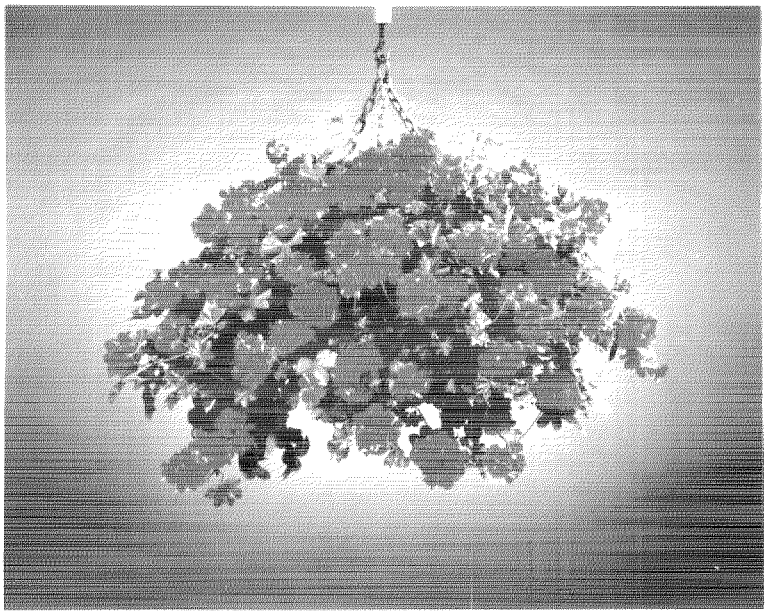

* * * * *